United States Patent [19]
Lin et al.

[11] Patent Number: 5,554,791
[45] Date of Patent: Sep. 10, 1996

[54] PROCESS FOR PRODUCING [S,S]-ETHYLENEDIAMINE-N,N'-DISUCCINIC ACID

[75] Inventors: Ronny W. Lin, Baton Rouge; Eldon E. Atkinson, Jr., Greenwell Springs; Donald E. Balhoff, Baton Rouge, all of La.

[73] Assignee: Albemarle Corporation, Richmond, Va.

[21] Appl. No.: 272,456

[22] Filed: Jul. 11, 1994

[51] Int. Cl.$^6$ .................................................. C07C 229/00
[52] U.S. Cl. ........................................................... 562/565
[58] Field of Search ............................................. 562/565

[56] References Cited

U.S. PATENT DOCUMENTS

| | | | |
|---|---|---|---|
| 3,158,635 | 11/1964 | Kezerian et al. | 260/429 |
| 4,704,233 | 11/1987 | Hartman et al. | 252/527 |

FOREIGN PATENT DOCUMENTS 558905   8/1977   U.S.S.R. .

OTHER PUBLICATIONS

Wagner, "Synthetic Organic Chemistry," pp. 666–670 & 715–727 (1953).
Neal, et al., "Stereospecific Ligands and Their Complexes. I. A Cobalt(III) Complex of Ethylenediaminedisuccinic Acid[1]", *Journal of Inorganic Chemistry*, vol. 7, No. 11, Nov., 1958, pp. 2405–2412.

*Primary Examiner*—Michael L. Shippen
*Attorney, Agent, or Firm*—E. E. Spielman, Jr.

[57] ABSTRACT

This invention relates to a process for selectively producing and recovering [S,S]-ethylenediamine-N,N'-disuccinic acid by the reaction of L-aspartic acid and 1,2-dihaloethane in an aqueous medium, wherein a stoichiometric deficiency of 1,2-dihaloethane is used and wherein the resultant aqueous solution obtained from the reaction is co-fed to water with a mineral acid to preferentially precipitate out [S,S]-ethylenediamine-N,N'-disuccinic acid from the solution.

31 Claims, No Drawings

PROCESS FOR PRODUCING [S,S]-ETHYLENEDIAMINE-N,N'-DISUCCINIC ACID

BACKGROUND OF THE INVENTION

This invention relates to a process for the selective production [S,S]-ethylenediamine-N,N'-disuccinic acid.

Ethylenediamine N,N'-disuccinic acid (EDDS) and its various alkali metal, alkaline earth metal, ammonium and substituted ammonium salts are well recognized by the detergent industry as useful chelating agents in cleaning formulations. (See U.S. Pat. No. 4,704,233, which is incorporated herein by reference as if fully set forth.) These salts and acids are theorized to chelate metals such as iron, manganese, copper and other multivalent metal ions. The metal ions are constituents of certain organic stains or act to stabilize such stains when present in washing solutions. Besides providing for the chelating function, EDDS and its salts are non-phosphorous compounds and, as a result, are environmentally desirable. Even further, EDDS and its salts exhibit biodegradability. The degree of biodegradability depends upon the optical EDDS isomer involved. Of the three optical isomers, [R,R], [R,S] and [S,S], the [S,S] isomer is most easily biodegradable and is thus preferred.

The [S,S] isomer can be synthesized from L-aspartic acid salt and 1,2-dibromoethane. A particularly attractive route features reacting sodium L-aspartate and 1,2-dibromoethane in an aqueous medium to yield, in solution, the sodium salts of [S,S] EDDS. See Neal and Rose, *Stereospecific Ligands and Their Complexes of Ethylenediamine-disuccinic Acid*, Inorganic Chemistry, Vol. 7. (1968), pp. 2405–2412. The Neal and Rose process reacts a fairly high percentage, say about 80%, of the L-aspartate in producing the sodium salt of [S,S] EDDS. This high conversion, however, does not translate into high selectivity for the [S,S] EDDS salt as the process produces a substantial amount of by-products. Thus, the ultimate recovered yield of [S,S] EDDS will be fairly low, e.g., 30% yield based on the L-aspartic acid initially present. The most common by-products are oligomers, 2-hydroxyethylamine N-succinic acid, and 2-bromoethylamine N-succinic acid.

The [S,S] EDDS salt produced by the Neal and Rose process is soluble in the reaction solution. To recover the salt from the solution, Neal and Rose teach that the reaction solution must be slowly acidified by adding concentrated hydrochloric acid to the solution to obtain a solution pH of 3.5. The acidification converts the [S,S] EDDS salt to [S,S] EDDS which crystallizes and precipitates from the solution. Fine crystals are said to precipitate out as the pH moves between pH 7 and 3.5. To purify the [S,S] EDDS precipitate, the precipitate is recovered and redissolved in a NaOH solution followed by reacidification. The cycle is repeated two times. The final precipitate is washed with water to remove HCl and any traces of L-aspartic acid.

While the Neal and Rose procedure may produce a relatively pure [S,S] EDDS product, it is burdened by (1) a high consumption of L-aspartic acid but with a low selectivity to obtain a low yield of recovered [S,S] EDDS (Neal and Rose reports the [S,S] EDDS yield at 25%), and (2) long process time and high HCl utilization, both due to the reacidification and redissolution cycles.

THE INVENTION

To obtain relatively pure [S,S] EDDS, a likewise pure salt of the acid is first produced. Accordingly, this invention provides a process for producing, with high selectivity, [S,S] EDDS salt. (The term "high selectivity" means that a majority, say >70%, of the L-aspartic acid reacted is converted to the desired salt.) Only a small amount, e.g., from about 5 to about 20 wt % of by-products is produced. The process comprises reacting L-aspartic acid and 1,2-dihaloethane in a basic aqueous medium, wherein there is a stoichiometric deficiency of 1,2-dihaloethane throughout the reaction period. The deficiency results in less than about 60 mole % of the initial L-aspartic acid being reacted. It is preferred that the total 1,2-dihaloethane to L-aspartic acid molar ratio be within the range of from about 0.1 to about 0.45:1, and most preferably within the range of from about 0.15 to about 0.35:1.

After the L-aspartic acid/1,2-dihaloethane reaction is completed, the reaction mass will comprise an aqueous solution which contains, water, alcohol (if used), unreacted L-aspartic acid (as a salt), [S,S] EDDS salt and minor amounts of various by-products. Since the amount of L-aspartic acid reacted was low, it is the predominate solute in the solution, with the [S,S] EDDS salt being the second most prevalent solute present. With a high L-aspartic acid salt concentration, the recovery of [S,S] EDDS from the aqueous solution becomes problematic as the simple addition of acid (as is done by Neal and Rose) to the aqueous solution will co-precipitate large amounts of L-aspartic acid along with the desired [S,S] EDDS.

It has now been discovered that the co-precipitation problem can be resolved by co-feeding, to a volume of water, (1) the aqueous solution and (2) an aqueous mineral acid having a dissociation constant within the range of from about $1.0 \times 10^{-5}$ to about $1.0 \times 10^{10}$, wherein the feed rates of the aqueous solution and the aqueous mineral acid are controlled so that the volume of water has a pH within the range of from about 2.0 to about 6.5 at least substantially throughout the co-feed period. It is preferred that the pH be within the range of from about 2.4 to about 5.5 and most highly preferred that the pH lie within the range of from about 2.6 to about 5.0. It is stated "substantially throughout the co-feed period" because there may be adjustment periods in which the pH may not be within the selected range, but these periods preferably do not exceed 25%, and most preferably 5%, of the co-feed period. Typically, the pH may be out of the selected range from about 10 seconds to 20 minutes.

The practice of the foregoing technique results in the production of an easily recoverable precipitate which contains up to about 99wt % [S,S] EDDS and less than 30 wt % L-aspartic acid. Since the selective production of the [S,S] EDDS salt, as described above, results in the presence of large amounts of L-aspartic acid, the [S,S] EDDS recovery technique is crucial to the commercial success of the overall process scheme.

DETAILED DESCRIPTION

Production of [S,S] EDDS Salt

The reaction of L-aspartic acid and 1,2-dihaloethane occurs in a basic aqueous medium. The medium is preferably water, but can contain lower alkanols, such as methanol, ethanol, isopropanol, butanol, etc. of these, ethanol is preferred. When an alkanol is used, the volume ratio of alkanol to water is within the range of from about 0.01:1 to about 1:1, and preferably within the range of from about 0.02:1 to about 0.4:1. In addition to the alkanols, other compounds can be present in the aqueous medium provided that they do not adversely affect the reaction of the L-aspartic acid and 1,2-dihaloethane or the solubility characteristics of the medium.

During the reaction, the basic aqueous medium will generally have a pH which lies within the range of from about 9 to about 13 and preferably within the range of from about 10 and 11. The pH values can be determined by the use of pH paper or any conventional pH meter.

It is convenient to render the aqueous medium basic by the use of a strong base. Exemplary are NaOH, KOH, LiOH, $Mg(OH)_2$ and $Ca(OH)_2$. Mixtures of any two or more of the foregoing are also suitable. Preferred are NaOH, KOH and $Ca(OH)_2$. In the basic medium, the L-aspartic acid and the [S,S] EDDS will be present as salts, with the salt cation being that provided by the base used to obtain the pH of the medium. Thus, for the preferred NaOH, the L-aspartic acid and the [S,S] EDDS will be present as the sodium salts. When the reaction of L-aspartic acid and 1,2-dihaloethane is referred to herein it is to be understood in the context of the basic medium in which the reaction takes place. The reactant is conventionally referred to as L-aspartic acid even though it is a salt in the basic medium in which the reaction occurs.

The L-aspartic acid is conveniently added to the basic medium as a solid. The addition should be performed with concern for the heat generated by the resultant neutralization. The medium can be cooled, the addition rate can be moderated or both can be used to handle tile rise in temperature. It is within the scope of this invention to add the L-aspartic acid as an aqueous solution, but care must be given to maintain the pH and concentration requirements of the process.

The 1,2-dihaloethane is preferably the bromo-, chloro-, or species with 1,2-dibromoethane and 1,2-dichloroethane being the most preferred.

Since it is desired to produce an essentially pure [S,S] EDDS, it is preferred that the L-aspartic acid and 1,2-dihaloethane be as pure as is practical for the reaction scale used.

The weight ratio of L-aspartic acid added to the basic medium preferably is within the range of from about 0.05:1 to about 1:1 and most preferably is within the range of from about 0.2:1 to about 0.8:1. The equivalent molar ratio of the basic medium to L-aspartic acid is preferably within the range of from about 0.5:1 to about 1.5:1 and most preferably is within the range of from about 0.7:1 to about 1.2:1. Other ratios can be used, the main consideration for any ratio being that the aqueous solution, which is obtained after the reaction is completed, will have the desired L-aspartate and [S,S] EDDS salt concentration for the practice of the [S,S] EDDS recovery technique described generally above and in more detail below. If an L-aspartic acid solution is used, then the amount of water introduced with the solution should be considered as added to the initial amount of basic medium used.

The aqueous solution can have a wide range of salt concentrations. Generally, the L-aspartic acid salt comprises from about 3 to about 50 wt % of the solution while the [S,S] EDDS salt comprises from about 2 to about 40 wt % of the solution. Preferably, the aqueous solution will have an L-aspartic acid salt concentration within the range of from about 5 to about 30 wt % of the solution and an [S,S] EDDS acid salt concentration within the range of from about 4 to about 25 wt % of the solution. All of the foregoing ranges provide suitable salt concentrations for the practice of the [S,S] EDDS recovery technique.

Recovery of [S,S] EDDS

As recited above [S,S] EDDS is recovered from the aqueous solution by co-feeding the solution and an aqueous mineral acid to a volume of water with the feed rates of the aqueous solution and the aqueous mineral acid being controlled so that the resultant pH for the volume of water will be within the range of from about 2 to about 6.5 at least substantially throughout the co-feed period.

Prior to its being co-fed to the volume of water, the aqueous solution will be basic. Generally, the aqueous solution will have a pH which is within the range of from about 8 to about 13, and most preferably within the range of from about 8.5 to about 12. When the solution salts are principally sodium salt, then the solution pH is preferably within the range of from about 8.5 to about 11.5.

The mineral acid aqueous solution should contain a sufficient concentration of the mineral acid so that, when it is co-fed with the aqueous salt solution at the desired rate, it will provide the selected pH. Many mineral acids can be chosen for the recovery technique. Exemplary acids are hydrohaloic acids, sulfuric acid, phosphoric acid, and mixtures of two or more of the foregoing. Hydrohaloic acids and sulfuric acid are preferred, with hydrochloric acid being most preferred. Preferred aqueous hydrochloric acid solutions are the concentrated solutions and more preferred are those which contain 2 to 40 wt % HCl. Most highly preferred are those containing from about 5 to about 37 wt % HCl.

The volume of water to which the aqueous solution and the aqueous mineral acid solution are co-fed serves many purposes. It acts as a mixing medium to effect the efficient mixing of the two co-fed solutions. Also, the volume of water acts as a crystallization medium which dilutes the two solutions as they are co-fed so that controlled precipitation is effected. Without dilution, supersaturation is possible. The volume of water also provides sufficient volume to dissipate the heat of neutralization. Even further, the volume of water provides sufficient water to hold the by-product salts of neutralization, e.g., NaCl, in solution so that they will not precipitate out. Finally, the volume of water provides for a sufficient volume so that the pH of the system can be conveniently measured, especially at the beginning of the co-feed. The size of the volume of water will increase over time as the two co-fed solutions bring water to the reaction system. Thus, with the volume of water ever increasing in size, the initial size of the volume of water is the main concern. The determination of a suitable initial water volume is best determined empirically with the goal being the accomplishment of the above recited functions. The empirical determination should consider the pH of the solutions co-fed, the salt or acid concentrations of the solutions co-fed, the volume feed rate of the co-fed solutions, and the precipitate quality desired. Generally speaking, the initial volume of water will provide a ratio of the water volume initially present before co-feed to the total volume of the solutions to be co-fed which lies within the range of from about 1:0.1 to about 1:5 and most preferably within the range of from about 1:0.2 to about 1:2.5. The size of the volume of water at any point during the co-feed period will be determined by the sum of the initial size of the volume of water and the amount of water introduced by the co-feed solutions, minus any water losses from the reaction system.

It is to be understood that the volume of water will ultimately contain various solutes, e.g., L-aspartate, inorganic salts and small amount of [S,S] EDDS. The identities and the concentrations of the solutes will change during the co-feed period. The [S,S] EDDS concentration will not increase dramatically as most all of it will be precipitating out of solution during the co-feed period.

By the term "co-feed" it is meant that the feeds of the aqueous solution and the aqueous mineral acid solution occur together timewise or in alternating portions. It is not a deviation from the method of this invention to start or finish one feed slightly before or after the other, or to have one feed interrupted for a short period of time, provided that the pH of the volume of water stays within the prescribed range for the prescribed period of time. The rate of feed for each solution is adjusted in response to maintaining the pH of the volume of water of the mix at the desired level. If the volume of water becomes too basic, then the mineral acid solution feed rate is increased or the aqueous solution feed rate is decreased. The reverse is true if the volume of water becomes too acidic. The alternating feed technique for effecting the co-feed features the intermittent addition of a portion of one of the feeds and then a portion of the other feed, with attention given to obtaining and maintaining the prescribed acidic pH substantially throughout the precipitation period. For example, a portion of the aqueous mineral acid is added until the prescribed water volume pH is obtained. Then a portion of the aqueous solution is added with care being taken to not leave the pH range. Another portion of the aqueous mineral acid is then added followed by another portion of the aqueous solution. The sequence is repeated until all of the acid and salt have been added.

The pH adjustments are made by measuring the pH of the water volume and, for these measurements, determining what adjustment, if any, is needed to obtain the desired pH. The pH values recited for the methods of this invention are obtained by the use of conventional pH meters with their probes located in the water volume. The meter which is suitable at a temperature of from 0° to 60° C.

The recovery method of this invention best occurs at any temperature at which the solutions and volume of water do not boil or freeze. It is preferred that the pressure be around ambient pressure. The temperature is preferably within the range of from about 5° to about 55° C.

After the co-feed is finished, a wet cake is formed by the recovery of precipitates from the volume of water. The recovery can be by filtration or centrifugation. After the recovery, the wet cake, which is essentially all [S,S] EDDS, is preferably washed with water to reduce the impurities content.

In its broadest definition, the separation technique, above described, accomplishes the selective precipitation of [S,S] EDDS over L-aspartic acid from an aqueous solution of the salts of these two acids by exposing the salts to a pH which is favorable to the precipitation of [S,S] EDDS over the precipitation of L-aspartic acid throughout substantially all of the period during which precipitation of either of the acids occur. It is stated "throughout substantially all of the period" because there may be an initial adjustment period in which the pH may stray, but that period is short and is measured in seconds to minutes, say 5 seconds to 10 minutes.

The following Examples are meant to illustrate the processes and techniques of this invention and are not to be taken as limiting the scope thereof.

The following Examples are of this invention.

EXAMPLE I 53.3 g of L-aspartic acid (0.40 g mole) and 100.3 g of water were charged into a 500 cc flask. 72.1 g of 44.1 wt % NaOH (0.80 g mole) aqueous solution were added to dissolve the acid. 20.3 g of EDB (0.108 g mole) were added. The reaction mass was heated up to 80° C. and stirred for 9 hours at atmospheric pressure. After the reactor was cooled down, 242.2 g of the reaction solution was obtained and had 11.83 wt % of L-AA and 10.04 wt % (45.9 normalized wt %) of [SS] EDDS by HPLC analysis. The conversion was about 46% with about 89.9% selectivity.

20 g of the reaction solution and 7.7 g of 18.25 wt % hydrochloric acid were co-fed to 37.4 g of water at a pH of 2.5–2.6 at ambient temperature. After the resultant slurry was filtered and washed with 35 g of water, 5.8 g of wet cake had 5.59 wt % of L-aspartic acid and 33.83 wt % (85.8 normalized wt %) of [SS] EDDS. (56.1 g of the filtrate (not including the wash) had 3.93 wt % of L-aspartic acid and 0.31 wt % (7.3 normalized wt %) of [SS] EDDS.

EXAMPLE II 20 g of the reaction solution (as in Example II) and 7 g of 18.25 wt % HCl solution were co-fed to 35 g of water at a pH of 2.7–2.8. After filtration and wash with 36 g water, the wet cake (2.5 g) had 0.95 wt % L-aspartic acid and 60.92 wt % (98.5 normalized wt %) [SS] EDDS while the mother liquor (57.3 g) had 6.48 wt % L-aspartic acid and 0.34 wt % (5.0 normalized wt %) [SS] EDDS.

EXAMPLE III 26.8 g of L-aspartic acid (0.20 g mole) and 100 g of water were charged into a 300 cc ss autoclave. 60 g of 25 wt % NaOH (0.38 g mole) aqueous solution were added to make aspartate solution. 5 g (0.05 g mole) of 1,2-dichloroethane (EDC) were added. After the reactor was purged with nitrogen, the reaction mixture was slowly heated up to 120° C. and reacted for 4.8 hours, during which the pressure in the autoclave was decreasing from ~50 to ~30 psig. 189 g of reaction solution were obtained (at ambient temperature). It contained 9.65 wt % L-aspartic acid (-31.9% conversion) and 44.44 wt % [SS] EDDS (~89.3% selectivity). Five additional runs were conducted with sodium L-aspartate and EDC for study at a temperature in 90°–110° C. range (with ~30–35% conversion and ~83—100% selectivity.)

1,110.3 g of above combined reaction solution (having 105.8 g of L-aspartic acid and 50.4 g of [SS] EDDS (32.3 normalized wt %)) and 189.2 g of 18.5 wt % hydrochloric acid were co-fed to 460 g of water at a pH of 3.95–3.95 at ambient temperature for 1.4 hours. The resultant slurry was stirred for 3 additional hours before being filtered. The wet cake (67.4 g), after washed with 60 g of water, had 0.76 wt % L-aspartic acid and 44.7 wt % [SS] EDDS (98.3 normalized wt %). The filtrate (1,668 g) had 5.77 wt% L-aspartic acid and 0.76 wt % [SS] EDDS (11.6 normalized wt %). The wash (64 g) had 3.58 wt % L-aspartic acid and 0.35 wt % [SS] EDDS (8.9 normalized wt %).

What is claimed:

1. A process for the production of [S,S]-ethylenediamine-N,N'-disuccinic acid, which process comprises:

a. reacting L-aspartic acid with a stoichiometric deficient amount of 1,2-dihaloethane in a basic aqueous medium to produce an aqueous solution containing from about 3 to about 50 wt % L-aspartic acid salt and from about 2 to about 40 wt % [S,S]-ethylenediamine-N,N'-disuccinic acid salt; and b. precipitating, from the aqueous solution, [S,S]-ethylenediamine-N,N'-disuccinic acid by co-feeding, to a volume of water, (1) the aqueous solution and (2) an aqueous mineral acid having a dissociation constant within the range of from about $1.0 \times 10^{-5}$ to about $1.0 \times 10^{10}$, wherein the feed rates of the aqueous solution and the aqueous mineral acid are controlled so that the volume of water has a pH within the range of from about 2 to about 6.5 at least substantially throughout the co-feed period.

2. The process of claim 1 wherein the 1,2-dihaloethane is 1,2-dibromoethane, 1,2-dichloroethane or a mixture thereof.

3. The method of claim 1 wherein the L-aspartic acid salt and the [S,S]-ethylenediamine-N,N'-disuccinic salt in the aqueous solution are the sodium salts.

4. The method of claim 1 wherein the mineral acid is a hydrohaloic acid.

5. The method of claim 1 wherein the aqueous mineral acid solution is a hydrochloric acid solution.

6. The method of claim 5 wherein the aqueous hydrochloric acid solution contains from about 2 to about 40 wt % HCl.

7. The method of claim 1 wherein the volume of water will provide a ratio of the water volume initially present before co-feed to the total volume of the solutions to be co-fed which lies within the range of from about 0.1 to about 5:1.

8. The method of claim 7 wherein the ratio is within the range of from about 0.2 to about 2.5:1.

9. The method of claim 1 wherein the pH is within the range of from about 2.4 to about 5.5.

10. The process of claim 1 wherein the pH during the co-feed is within the range of from about 2.6 to about 5.0.

11. A process for the production of [S,S]-ethylenediamine-N,N'-disuccinic acid, which process comprises:

a. reacting L-aspartic acid and 1,2-dihaloethane in a basic aqueous medium wherein there is a stoichiometric deficiency of the 1,2-dihaloethane throughout the reaction period so that less than 60 mole % of the L-aspartic acid is reacted to yield an aqueous solution containing unreacted L-aspartic acid salt and [S,S]-ethylenediamine-N,N'-disuccinic acid salt; and b. precipitating, from the aqueous solution, [S,S]-ethylenediamine-N,N'-disuccinic acid by co-feeding, to a volume of water, (1) the aqueous solution and (2) an aqueous mineral acid having a dissociation constant within the range of from about $1.0 \times 10^{-5}$ to about $1.0 \times 10^{10}$ wherein the feed rates of the aqueous solution and the aqueous mineral acid are controlled so that the volume of water has a pH within the range of from about 2 to about 6.5 at least substantially throughout the co-feed period.

12. The method of claim 11 wherein the L-aspartic acid salt and the [S,S]-ethylenediamine-N,N'-disuccinic salt in the aqueous solution are the sodium salts.

13. The method of claim 11 wherein the mineral acid is a hydrohaloic acid.

14. The method of claim 11 wherein the aqueous mineral acid solution is a hydrocholoric acid solution.

15. The method of claim 14 wherein the aqueous hydrochloric acid solution contains from about 2 to about 40 wt % HCl.

16. The method of claim 11 wherein the volume of water will provide a ratio of the water volume initially present before co-feed to the total volume of the solutions to be co-fed which lies within the range of from about 0.1 to about 5:1.

17. The method of claim 16 wherein the ratio is within the range of from about 0.2 to about 2.5:1.

18. The method of claim 11 wherein the pH is within the range of from about 2.4 to about 5.5.

19. The method of claim 11 wherein the pH during the co-feed is within the range of from about 2.6 to about 5.0.

20. A process for the production of [S,S]-ethylenediamine-N,N'-disuccinic acid, which process comprises:

a. reacting 1,2-dihaloethane and L-aspartic acid in a basic aqueous medium wherein the 1,2-dihaloethane to L-aspartic acid molar ratio is within the range of from about 0.1 to about 0.45:1 to yield an aqueous solution containing unreacted L-aspartic acid salt and [S,S]-ethylenediamine-N,N'-disuccinic acid salt; and b. precipitating, from the aqueous solution, [S,S]-ethylenediamine-N,N'-disuccinic acid by co-feeding, to a volume of water, (1) the aqueous solution and (2) an aqueous mineral acid having a dissociation constant within the range of from about $1.0 \times 10^{-5}$ to about $1.0 \times 10^{10}$, wherein the feed rates of the aqueous solution and the aqueous mineral acid are controlled so that the volume of water has a pH within the range of from about 2 to about 6.5 at least substantially throughout the co-feed period.

21. The process of claim 20 wherein the molar ratio is within the range of from about 0.15 to about 0.35:1.

22. The process of claim 20 wherein the 1,2-dihaloethane is 1,2-dibromoethane, 1,2-dichloroethane or a mixture thereof.

23. The process of claim 20 wherein the process yields an aqueous solution containing from about 3 to about 50 wt % L-aspartic acid salt and from about 2 to about 40 wt % [S,S] EDDS salt, the percentages being based upon the total weight of the solution.

24. The method of claim 20 wherein the L-aspartic acid salt and the [S,S]-ethylenediamine-N,N'-disuccinic salt in the aqueous solution are the sodium salts.

25. The method of claim 20 wherein the mineral acid is a hydrohaloic acid.

26. The method of claim 20 wherein the aqueous mineral acid solution is a hydrochloric acid solution.

27. The method of claim 26 wherein the aqueous hydrochloric acid solution contains from about 2 to about 40 wt % HCl.

28. The method of claim 20 wherein the volume of water will provide a ratio of the water volume initially present before co-feed to the total volume of the solutions to be co-fed which lies within the range of from about 0.1 to about 5:1.

29. The method of claim 28 wherein the ratio is within the range of from about 0.2 to about 2.5:1.

30. The method of claim 20 wherein the pH is within the range of from about 2.4 to about 5.5.

31. The method of claim 20 wherein the pH is within the range of from about 2.6 to about 5.0.

* * * * *